United States Patent
Yeo et al.

(10) Patent No.: US 7,613,486 B2
(45) Date of Patent: Nov. 3, 2009

(54) METHOD AND APPARATUS FOR EVALUATING HUMAN STRESS USING PHOTOPLETHYSMOGRAPHY

(75) Inventors: Hyung-sok Yeo, Suwon-si (KR); Jeong-whan Lee, Suwon-si (KR); Gil-won Yoon, Seoul (KR); Hyun-tai Hwang, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 921 days.

(21) Appl. No.: 10/760,544

(22) Filed: Jan. 21, 2004

(65) Prior Publication Data
US 2004/0220483 A1  Nov. 4, 2004

(30) Foreign Application Priority Data
Jan. 22, 2003  (KR)  .......... 10-2003-0004256

(51) Int. Cl.
*A61B 5/00*  (2006.01)
*A61B 5/02*  (2006.01)

(52) U.S. Cl. .............. 600/310; 600/300; 600/481; 600/500

(58) Field of Classification Search .............. None
See application file for complete search history.

(56) References Cited

U.S. PATENT DOCUMENTS

| | | | |
|---|---|---|---|
| 4,759,366 A * | 7/1988 | Callaghan | 607/26 |
| 4,867,165 A | 9/1989 | Noller et al. | |
| 4,907,596 A * | 3/1990 | Schmid et al. | 600/485 |
| 5,267,568 A * | 12/1993 | Takara | 600/500 |
| 5,297,548 A | 3/1994 | Polage et al. | |
| 5,413,101 A * | 5/1995 | Sugiura | 600/323 |
| 5,830,131 A | 11/1998 | Caro et al. | 600/300 |
| 6,117,075 A | 9/2000 | Barnea et al. | 600/300 |
| 6,261,236 B1 * | 7/2001 | Grimblatov | 600/500 |
| 6,280,390 B1 * | 8/2001 | Akselrod et al. | 600/485 |
| 6,340,346 B1 | 1/2002 | Almog et al. | 600/300 |
| 6,496,723 B1 * | 12/2002 | Kawachi et al. | 600/517 |
| 2003/0163050 A1 | 8/2003 | Dekker | |

FOREIGN PATENT DOCUMENTS

| | | |
|---|---|---|
| JP | 9-294724 | 11/1997 |
| JP | 2000-116614 | 4/2000 |
| WO | WO 03/071938 | 9/2003 |

OTHER PUBLICATIONS

Patent Abstract of Japan, 10071137, Mar. 17, 1998, Yoshiro, "Device and Method for Displaying Degree of Stress".
Patent Abstracts of Japan, 2000333919, Dec. 5, 2000, Shinichi, "Organism Information Measuring Device".

* cited by examiner

*Primary Examiner*—Patricia C Mallari
(74) *Attorney, Agent, or Firm*—Lee & Morse, P.C.

(57) ABSTRACT

A method of evaluating human stress using photoplethysmography (PPG) includes defining at least one PPG parameter, radiating light having at least one wavelength, which reacts to a blood component to be measured, at a measuring target and measuring a PPG signal from the measuring target during a predetermined period of time, and evaluating a level of human stress using a plurality of stress indexes obtained from the PPG parameter.

24 Claims, 8 Drawing Sheets

METHOD AND APPARATUS FOR EVALUATING HUMAN STRESS USING PHOTOPLETHYSMOGRAPHY

BACKGROUND OF THE INVENTION

1. Field of the Invention

The present invention relates to evaluating human stress. More particularly, the present invention relates to a method and apparatus for evaluating human stress using photoplethysmography (PPG).

2. Description of the Related Art

In the field of medical diagnosis, there have been various attempts to diagnose cardiovascular diseases, detect a degree of development of a disease, or detect a stiffness of a blood vessel using PPG. PPG indicates a signal corresponding to a quantity of light reflected from a selected part of a human body after being irradiated by light having a particular wavelength emitted from a light source of a light emitting device. Technology using PPG has been primarily developed for the purpose of determining a patient's physiological condition of an arterial system but may be used as an auxiliary means for diagnosing particular diseases.

Conventional apparatuses and methods using PPG have been developed to measure a patient's physiological condition, a condition of a fetus, and a depth of an anesthesia. In addition, a variety of methods using various types of physiological signals to which a human body reacts have been proposed to evaluate human pleasantness, human tranquility, or human stress. In these methods, human stress or pleasantness is measured and evaluated based on at least two physiological signals. In other words, in order to evaluate or continuously monitor the condition of a human body, various physiological signals such as ECG, EEG, EMG, PPG, GSR, and SKT are collected and analyzed.

There are various conventional technologies that may provide reliable analysis results by collecting various physiological signals. However, often there are many restrictions on human subjects along with a requirement of a large scale of a system. For example, a measurement itself often affects a human subject by increasing the subject's level of stress. Moreover, if a glove type or finger contact type measuring devices is used in order to obtain PPG from a human subject's fingers, the human subject is restricted from performing manual operations, such as working on a personal computer (PC) and other operations that require use of the patient's hand.

SUMMARY OF THE INVENTION

The present invention provides a method and apparatus for evaluating a level of stress in a human subject, i.e., a degree of tranquility, using an amplitude of a pulse component of a photoplethysmography (PPG), a change in a baseline, and a variation in a peak-to-peak interval of the PPG generated in accordance with a heart rate.

According to a feature of an embodiment of the present invention, there is provided a method of evaluating human stress using photoplethysmography (PPG) including defining at least one PPG parameter, radiating light having at least one wavelength, which reacts to a blood component to be measured, at a measuring target and measuring a PPG signal from the measuring target during a predetermined period of time, and evaluating a level of human stress using a plurality of stress indexes obtained from the PPG parameter.

In the method, the at least one PPG parameter may be selected from the group consisting of a pulse component amplitude, a peak-to-peak interval, and a baseline spread range. Evaluating the level of human stress may include using one of a long-term test and a short-term test.

In an embodiment of the present invention, evaluating the level of human stress may include obtaining an average of pulse component amplitudes during a predetermined period of time, comparing a baseline spread range with the average of pulse component amplitudes during the predetermined period of time, and calculating a relative stress index based on a relationship between the baseline spread range and the average of pulse component amplitudes.

In an embodiment of the present invention, evaluating the level of human stress in the short-term test may include obtaining an average of peak-to-peak intervals during a predetermined period of time, counting a number of peak-to-peak intervals less than the average peak-to-peak interval and a number of peak-to-peak intervals greater than the average peak-to-peak interval, during the predetermined period of time, and calculating a relative stress index based on a relationship between the number of peak-to-peak intervals less than the average peak-to-peak interval and the number of peak-to-peak intervals greater than the average peak-to-peak interval.

In an embodiment of the present invention, evaluating the human stress in the long-term test may include obtaining peak-to-peak intervals with respect to all pulses during a predetermined period of time, defining a plurality of data groups composed of a predetermined number of peak-to-peak intervals with respect to all of the peak-to-peak intervals obtained during the predetermined period of time, performing a predetermined statistical method according to a number of the plurality of data groups, and calculating a stress index based on a p-value detected as a result of performing the predetermined statistical method. Preferably, the predetermined statistical method is a two-sample paired t-test when the number of the plurality of data groups is two and is one-way ANalysis Of VAriance (ANOVA) when the number of the plurality of data groups is three or more.

In another embodiment of the present invention, evaluating the level of human stress in the short-term test may include obtaining an average of pulse component amplitudes during a predetermined period of time; counting a number of pulse components having an amplitude less than the average of pulse component amplitudes and a number of pulse components having an amplitude greater than the average of pulse component amplitudes, during the predetermined period of time, and calculating a relative stress index based on a relationship between the number of pulse components having an amplitude less than the average of pulse component amplitudes and the number of pulse components having an amplitude greater than the average of pulse component amplitudes.

In another embodiment of the present invention, evaluating the level of human stress in the long-term test may include obtaining pulse component amplitudes with respect to all pulses during a predetermined period of time, defining a plurality of data groups composed of a predetermined number of pulse component amplitudes with respect to all of the pulse component amplitudes obtained during the predetermined period of time, performing a predetermined statistical method according to a number of the plurality of data groups, and calculating a stress index based on a p-value detected as a result of performing the predetermined statistical method. Preferably, the predetermined statistical method is a two-sample paired t-test when the number of the plurality of data groups is two and is one-way ANalysis Of VAriance (ANOVA) when the number of the plurality of data groups is three or more.

In the method, evaluating the level of human stress may include obtaining an average of pulse component amplitudes and an average peak-to-peak interval during a predetermined period of time, comparing a baseline spread range with the average of pulse component amplitudes during the predetermined period of time, calculating a relative first stress index based on a relationship between the baseline spread range and the average of pulse component amplitudes, counting a total number of peak-to-peak intervals, a number of peak-to-peak intervals less than the average peak-to-peak interval, and a number of peak-to-peak intervals greater than the average peak-to-peak interval, during the predetermined period of time, and calculating a relative second stress index based on a relationship between the number of peak-to-peak intervals less than the average peak-to-peak interval and the number of peak-to-peak intervals greater than the average peak-to-peak interval.

Evaluating the level of human stress may further include counting a total number of pulse components, a number of pulse components having an amplitude less than the average of pulse component amplitudes, and a number of pulse components having an amplitude greater than the average of pulse component amplitudes, during the predetermined period of time, and calculating a relative third stress index based on a relationship between the number of pulse components having an amplitude less than the average of pulse component amplitudes and the number of pulse components having an amplitude greater than the average of pulse component amplitudes.

The method may further include averaging the plurality of stress indexes acquired using at least one PPG parameter and determining an average stress index as a final stress index.

The method may further include performing low-pass filtering to remove high-frequency noise from the measured PPG signal, before evaluating the level of human stress.

The method may further include displaying the plurality of stress indexes and the evaluated level of human stress obtained during evaluating the level of human stress.

According to another feature of an embodiment of the present invention, there is provided a computer-readable recording medium including a first program for defining photoplethysmography (PPG) parameters including at least one of a pulse component amplitude, a peak-to-peak interval, and a baseline spread range recorded on the medium, a second program for radiating light having at least one wavelength, which reacts to a blood component to be measured, at a measuring target and measuring a PPG signal from the measuring target for a predetermined period of time recorded on the medium, and a third program for evaluating a level of human stress based on the PPG parameters defined by the first program, in one of a long-term test and a short-term test, which are identified depending on a measuring time of the PPG signal, recorded on the medium.

According to yet another feature of an embodiment of the present invention, there is provided an apparatus for evaluating human stress using photoplethysmography (PPG) including a PPG measuring unit, which radiates light having at least one wavelength, which reacts to a blood component to be measured, at a measuring target and measures a PPG signal from the measuring target during a predetermined period of time, an amplifying and filtering unit, which amplifies the PPG signal provided from the PPG measuring unit to a predetermined level and performs filtering to remove noise components, and a signal processing unit, which defines at least one PPG parameter and evaluates a level of human stress using a plurality of stress indexes acquired using the PPG parameter.

The PPG parameter may be at least one selected from the group consisting of a pulse component amplitude, a peak-to-peak interval, and a baseline spread range.

The level of human stress may be acquired from one of a long-term test and a short-term test, which are identified depending on a measuring time of the PPG signal provided from the amplifying and filtering unit.

The PPG measuring unit preferably has a block letter "C" shape so that the measuring target can be inserted into the PPG measuring unit, and has a transmissive or a reflective structure.

The signal processing unit may include a first function of obtaining an average of pulse component amplitudes and an average peak-to-peak interval during the predetermined period of time, a second function of comparing a baseline spread range with the average of pulse component amplitudes during the predetermined period of time, and a third function of calculating a relative first stress index based on a relationship between the baseline spread range and the average of pulse component amplitudes.

The signal processing unit may further include a fourth function of counting a total number of peak-to-peak intervals, a number of peak-to-peak intervals less than the average peak-to-peak interval, and a number of peak-to-peak intervals greater than the average peak-to-peak interval, during the predetermined period of time and a fifth function of calculating a relative second stress index based on a relationship between the number of peak-to-peak intervals less than the average peak-to-peak interval and the number of peak-to-peak intervals greater than the average peak-to-peak interval.

The signal processing unit may further include a sixth function of counting a total number of pulse components, a number of pulse components having an amplitude less than the average of pulse component amplitudes, and a number of pulse components having an amplitude greater than the average of pulse component amplitudes, during the predetermined period of time and a seventh function of calculating a relative third stress index based on a relationship between the number of pulse components having an amplitude less than the average of pulse component amplitudes and the number of pulse components having an amplitude greater than the average of pulse component amplitudes.

The signal processing unit may further include an eighth function of averaging the plurality of stress indexes acquired from one of the long- and short-term tests based on the PPG parameters and determining an average stress index as a final stress index.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Figure 1:
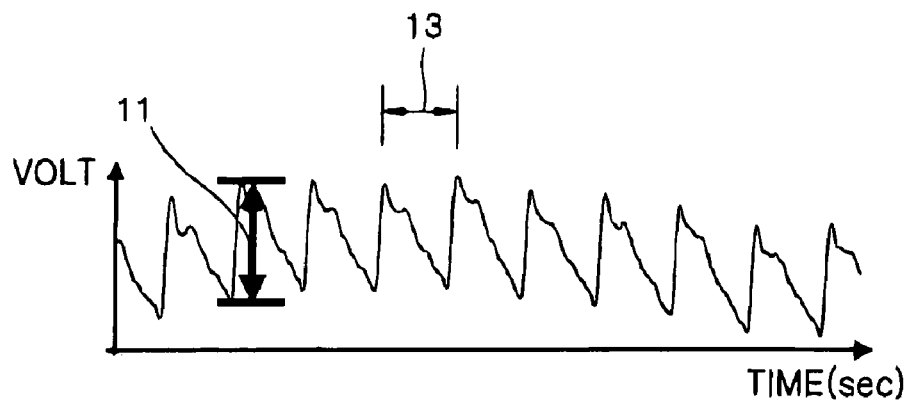
FIG. 1 is a graph illustrating a pulse component and a peak-to-peak interval in a photoplethysmography (PPG) signal.

Korean Patent Application No. 2003-4256, filed on Jan. 22, 2003, and entitled: "Method and Apparatus for Evaluating Human Stress Using Photoplethysmography," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

Information about a degree of contraction of a peripheral blood vessel and an increase or decrease in a cardiac output is reflected by photoplethysmography (PPG). The degree of contraction of a peripheral blood vessel and the increase or decrease in the cardiac output are dominated by an autonomic nervous system controlling a myocardial motion. For example, when a sympathetic nerve is excited by an external stimulus, a cardiac function, such as heart rate (HR), increases, a stimulus conduction rate increases or excitability increases, and contractility is accentuated. An HR, or pulse, indicates the number of times a heart pulses per one minute and is expressed as beats per minute (BPM). Normal adults have an HR of 60-90 BPM. An HR increases during exercise, mental excitement, or fever and decreases during sleep. More specifically, when a sympathetic nerve is excited, a peak-to-peak interval of PPG decreases due to an increase in HR, and the amplitude of a pulse component of PPG decreases due to a contraction of a peripheral blood vessel.

In addition, a baseline in PPG changes due to an irregular deep breath or other moving artifact made by a human subject not at rest. In a change in HR during breathing, the HR increases during inhalation due to an acceleration in the motion of a sinoatrial node and decreases during exhalation. With a change in the baseline in PPG, a peak-to-peak interval repeatedly increases and decreases, and increasing and decreasing degrees thereof and status vary depending on a degree of stimulus to the sympathetic nerve.

FIG. 1 is a graph illustrating a pulse component and a peak-to-peak interval (PPI) in a PPG signal collected from a human subject. In the graph, a height from a lowest point to a highest point in each pulse is referred to as a pulse component amplitude 11. A distance between adjacent highest points is referred to as a peak-to-peak interval 13.

Figure 2A:
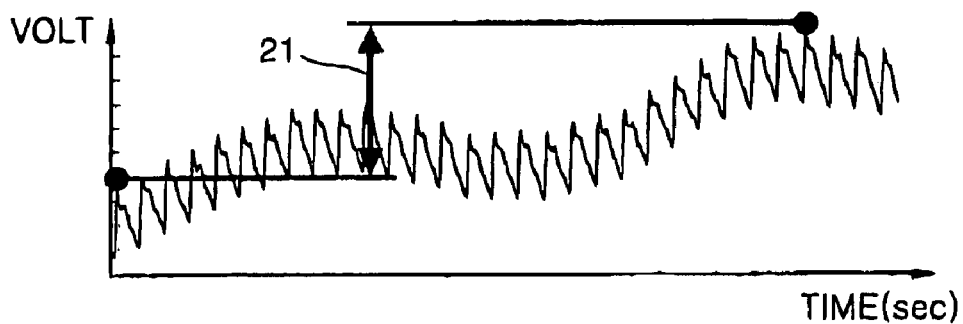
FIGS. 2A and 2B are graphs illustrating the spread range of a baseline in a PPG signal.
Figure 2B:
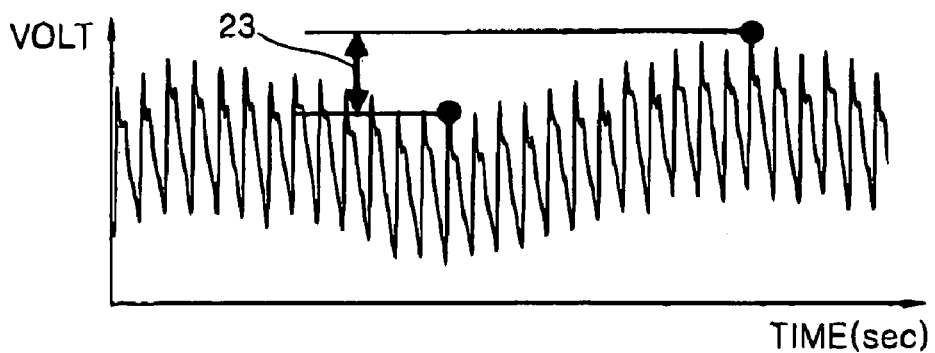

FIGS. 2A and 2B are graphs illustrating a spread range of a baseline in a PPG signal. The spread range of a baseline is expressed by a difference between a highest peak value and a lowest peak value in the entire collected data. The spread range of a baseline reflects information on a change in the PPG baseline. A baseline spread range 21 appearing when an irregular breath or other moving artifact occurs, as shown in FIG. 2A, is greater than a baseline spread range 23 appearing when breathing or posture is stable, as shown in FIG. 2B. Thus, it may be inferred that a change in a baseline is minimized when breathing or posture is stable.

Figure 3A:
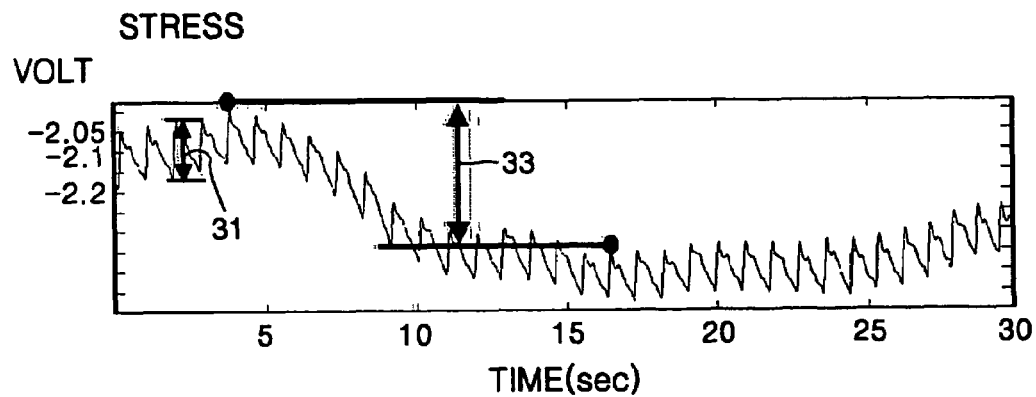
FIGS. 3A and 3B are graphs showing changes in PPG signals during conditions of stress and resting, respectively.
Figure 3B:
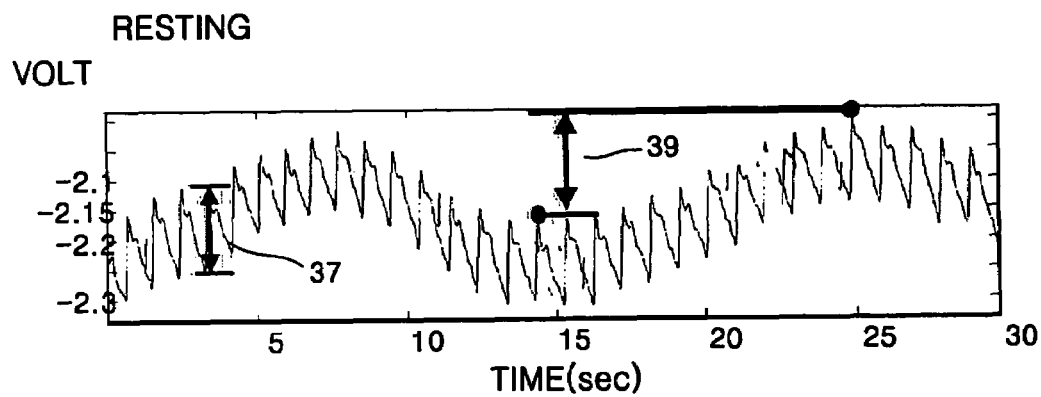

FIGS. 3A and 3B are graphs showing changes in PPG signals during conditions of stress and resting, respectively. A pulse component amplitude 31 during stress is less than a pulse component amplitude 37 during resting, and a baseline spread range 33 during stress is greater than a baseline spread range 39 during resting.

Figure 4:
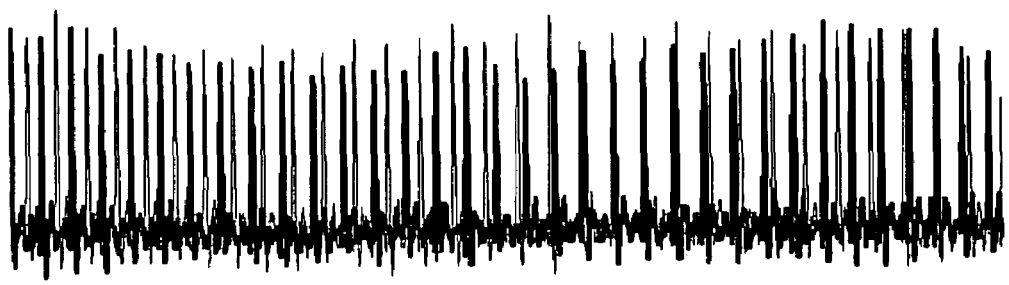
FIG. 4 is a graph showing the results of differentiating the PPG signal shown in FIG. 3A and the PPG signal shown in FIG. 3B.

FIG. 4 is a graph showing results of primarily differentiating the PPG signal shown in FIG. 3A and the PPG signal shown in FIG. 3B in order to closely compare changes in a pulse component amplitude between conditions of stress and resting. Since primary differentiation removes direct current components from the PPG signals, only the pulse components can be easily compared. It may be seen from FIG. 4 that the pulse component amplitude during stress is reduced as compared to the pulse component amplitude during resting.

Experiments were repeatedly performed on five human subjects in order to verify whether there was a statistically significant difference in an average of pulse component amplitudes in PPG, i.e., an AC mean, between conditions of stress and resting, as shown in FIG. 4. Here, for a light source used to collect PPG signals, five particular wavelengths within a range of 500-1000 nm were selected and referred to as AC1, AC2, AC3, AC4, and AC5, respectively. After collecting PPG data with respect to the five wavelengths, pulse component amplitudes were extracted and configured into a data set. Then, a paired t-test was performed with respect to two groups in a stress condition and a resting condition, respectively. The results of the experiments are shown in Table 1.

TABLE 1

| Human subject | Wavelength | Stress AC mean | Stress AC Sd | Resting AC mean | Resting AC Sd | p-value |
|---|---|---|---|---|---|---|
| #1-1 | AC1 | 134.77 | 12.28 | 144.21 | 13.00 | 0.005 |
|  | AC2 | 90.87 | 10.79 | 96.59 | 7.57 | 0.026 |
|  | AC3 | 132.79 | 17.03 | 138.82 | 10.05 | 0.017 |
|  | AC4 | 127.44 | 13.02 | 133.26 | 7.32 | 0.034 |
|  | AC5 | 130.33 | 13.54 | 138.95 | 10.60 | 0.031 |
| #1-2 | AC1 | 125.79 | 15.23 | 150.34 | 12.95 | 0.000 |
|  | AC2 | 86.37 | 16.10 | 90.63 | 9.18 | 0.175 |
|  | AC3 | 120.11 | 15.68 | 140.79 | 11.52 | 0.000 |
|  | AC4 | 112.87 | 14.43 | 138.97 | 11.59 | 0.000 |
|  | AC5 | 119.08 | 17.18 | 134.24 | 11.41 | 0.000 |
| #1-3 | AC1 | 139.44 | 16.15 | 153.51 | 14.03 | 0.001 |
|  | AC2 | 88.37 | 11.37 | 93.98 | 11.05 | 0.046 |
|  | AC3 | 131.61 | 15.44 | 142.15 | 14.00 | 0.007 |
|  | AC4 | 130.27 | 13.80 | 138.39 | 13.17 | 0.025 |
|  | AC5 | 125.54 | 15.64 | 135.68 | 14.03 | 0.015 |
| #2-1 | AC1 | 178.29 | 13.10 | 198.26 | 15.97 | 0.000 |
|  | AC2 | 117.74 | 12.52 | 133.43 | 11.39 | 0.000 |
|  | AC3 | 178.06 | 12.22 | 200.23 | 16.23 | 0.000 |
|  | AC4 | 164.23 | 10.97 | 183.40 | 12.21 | 0.000 |
|  | AC5 | 170.83 | 12.09 | 193.03 | 13.68 | 0.000 |
| #2-2 | AC1 | 198.32 | 14.18 | 210.62 | 10.04 | 0.000 |
|  | AC2 | 135.21 | 11.01 | 140.71 | 7.61 | 0.019 |
|  | AC3 | 200.35 | 14.59 | 207.94 | 14.29 | 0.044 |
|  | AC4 | 186.15 | 13.99 | 191.62 | 11.97 | 0.101 |
|  | AC5 | 189.65 | 12.92 | 196.71 | 10.13 | 0.022 |
| #2-3 | AC1 | 198.50 | 12.95 | 216.38 | 12.56 | 0.000 |
|  | AC2 | 135.21 | 9.78 | 145.41 | 8.17 | 0.000 |
|  | AC3 | 199.41 | 11.91 | 215.12 | 13.34 | 0.000 |

TABLE 1-continued

| Human subject | Wavelength | Stress AC mean | Stress AC Sd | Resting AC mean | Resting AC Sd | p-value |
|---|---|---|---|---|---|---|
| | AC4 | 183.85 | 10.91 | 193.00 | 13.29 | 0.003 |
| | AC5 | 187.68 | 10.63 | 198.74 | 12.23 | 0.000 |
| #3-1 | AC1 | 227.79 | 16.70 | 241.21 | 15.79 | 0.002 |
| | AC2 | 138.45 | 12.27 | 154.89 | 13.15 | 0.000 |
| | AC3 | 217.03 | 14.69 | 226.55 | 13.89 | 0.013 |
| | AC4 | 214.05 | 16.28 | 232.00 | 15.69 | 0.000 |
| | AC5 | 206.87 | 15.39 | 219.47 | 15.93 | 0.002 |
| #3-2 | AC1 | 212.59 | 15.42 | 220.76 | 12.48 | 0.019 |
| | AC2 | 137.43 | 13.93 | 145.35 | 11.93 | 0.004 |
| | AC3 | 205.27 | 16.48 | 210.51 | 15.60 | 0.127 |
| | AC4 | 208.41 | 13.57 | 214.19 | 11.94 | 0.028 |
| | AC5 | 198.89 | 13.92 | 204.73 | 15.79 | 0.041 |
| #4-1 | AC1 | 478.58 | 19.78 | 529.92 | 23.33 | 0.000 |
| | AC2 | 232.83 | 14.10 | 274.23 | 15.89 | 0.000 |
| | AC3 | 392.63 | 19.03 | 451.33 | 21.58 | 0.000 |
| | AC4 | 470.93 | 23.90 | 527.45 | 22.12 | 0.000 |
| | AC5 | 466.33 | 20.28 | 526.83 | 24.48 | 0.000 |
| #5-1 | AC1 | 462.78 | 24.58 | 482.96 | 28.65 | 0.017 |
| | AC2 | 246.89 | 15.20 | 262.93 | 15.77 | 0.005 |
| | AC3 | 406.41 | 20.62 | 428.19 | 24.95 | 0.005 |
| | AC4 | 440.15 | 18.61 | 459.81 | 21.70 | 0.005 |
| | AC5 | 390.70 | 20.55 | 410.78 | 24.24 | 0.012 |
| #5-2 | AC1 | 484.04 | 17.10 | 513.68 | 14.69 | 0.000 |
| | AC2 | 260.68 | 16.83 | 290.86 | 14.89 | 0.000 |
| | AC3 | 428.50 | 17.03 | 451.71 | 18.41 | 0.000 |
| | AC4 | 462.32 | 14.71 | 486.79 | 15.95 | 0.000 |
| | AC5 | 414.18 | 16.22 | 434.07 | 13.09 | 0.000 |
| #5-3 | AC1 | 417.52 | 34.39 | 468.62 | 24.36 | 0.000 |
| | AC2 | 222.72 | 20.10 | 263.38 | 18.11 | 0.000 |
| | AC3 | 366.83 | 28.67 | 414.86 | 20.27 | 0.000 |
| | AC4 | 395.03 | 32.38 | 443.62 | 21.24 | 0.000 |
| | AC5 | 365.38 | 27.06 | 405.90 | 16.92 | 0.000 |

Referring to Table 1, when the two groups are compared, most p-values are less than 0.05, that is, it is determined that there is a statistically significant difference in most cases. Even in cases where p-values exceed 0.05, it may be seen that an AC mean during stress is less than that at rest.

Table 2 shows relationships among PPG parameters defined by the present invention and a human subject's stress and resting conditions.

TABLE 2

| | PPG parameters | | |
|---|---|---|---|
| Conditions | Pulse component amplitude | PPI | Baseline spread range |
| Strain, Stress, Irregular breathing, Moving artifact | ↓ | ↓ | ↑ |
| Tranquil, Resting, Regular breathing, Stable posture | ↑ | ↑ | ↓ |

Figure 5:
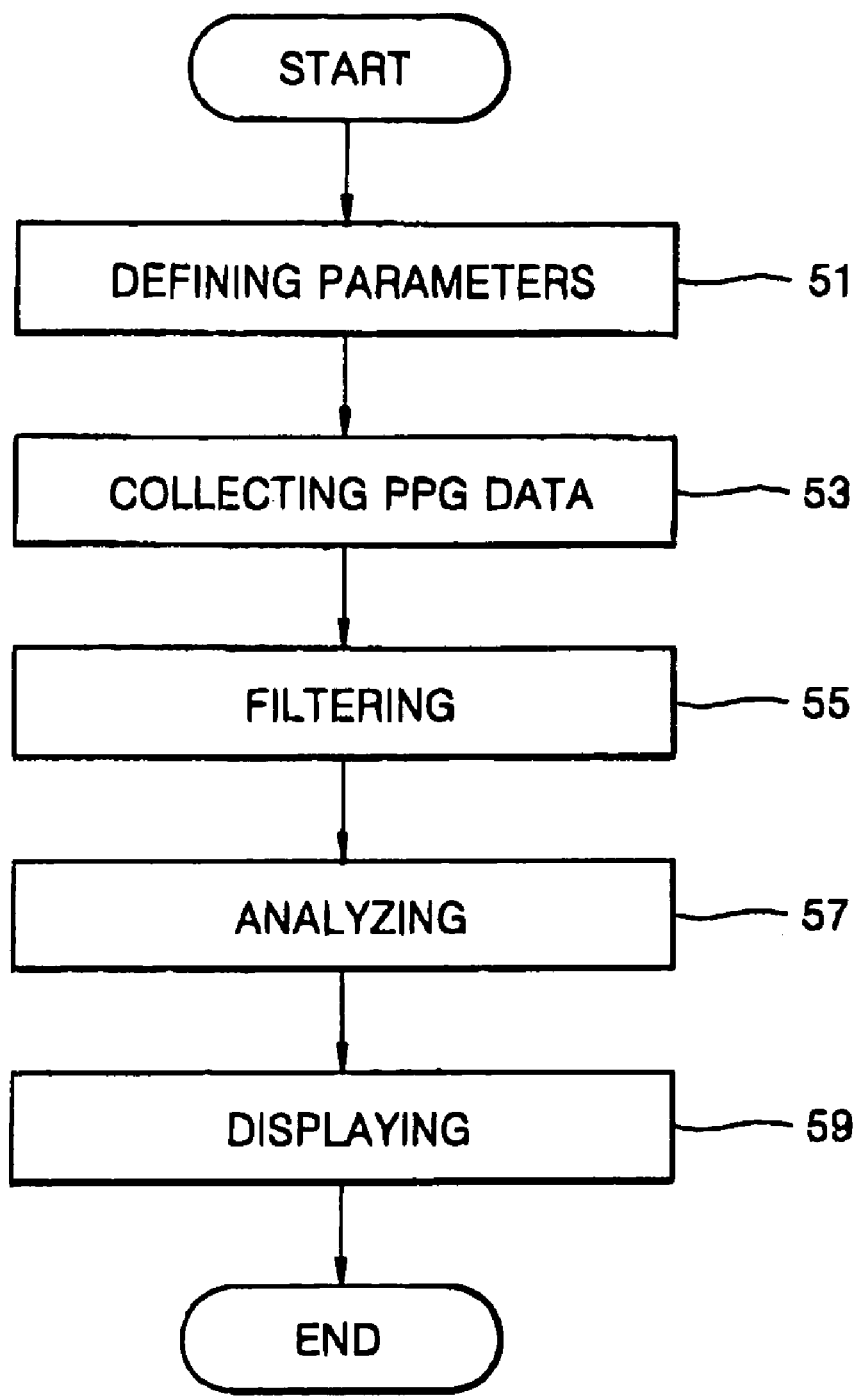
FIG. 5 is a flowchart of a method of evaluating human stress using PPG according to an embodiment of the present invention.

FIG. 5 is a flowchart of a method of evaluating human stress using PPG according to an embodiment of the present invention. The method includes defining parameters in step 51, collecting PPG data in step 53, filtering in step 55, analyzing in step 57, and displaying in step 59.

Figure 6:
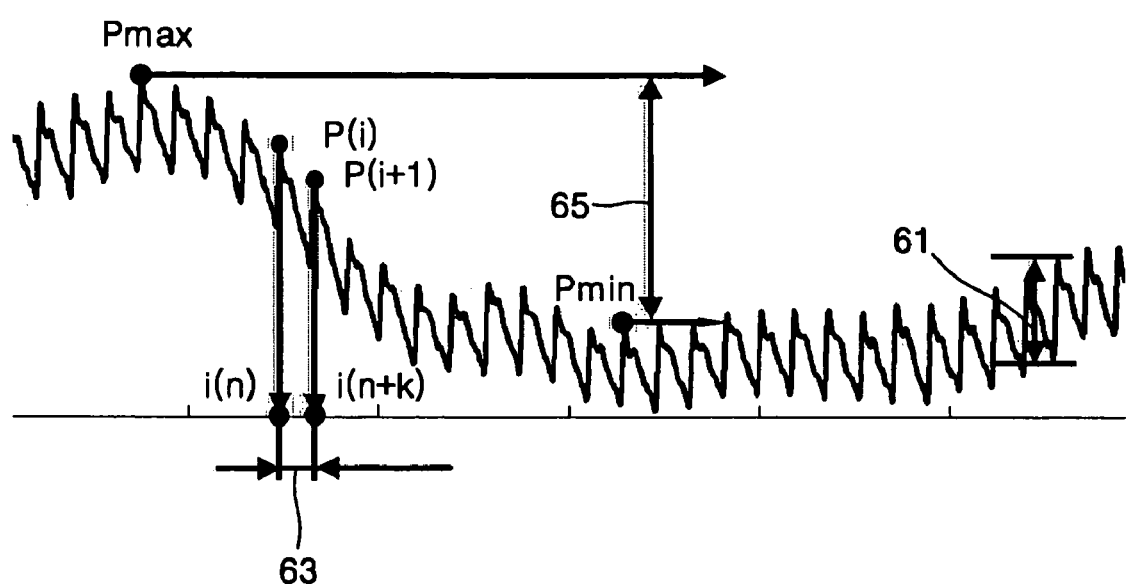
FIG. 6 is a graph illustrating parameters defined in the method shown in FIG. 5.

Referring to FIG. 5, in step 51, PPG parameters are defined, as shown in FIG. 6. Referring to FIG. 6, a pulse component amplitude 61 is defined by a difference between a highest point and a lowest point of each pulse. In association with the pulse component amplitude 61, an AC mean and a total number of pulse components per a predetermined period of time are defined. In the total number of pulse components, the number of pulse components having an amplitude less than the AC mean is defined as a "small AC count". A ratio of the small AC count to the total number of pulse components is defined as a "small AC count %". A value obtained by subtracting the small AC count % from 100 is defined as a "large AC count %".

Next, an i-th PPI 63 is defined by a time interval between an i-th peak P(i) and an adjacent (i+1)-th peak P(i+1) and is represented by PPI (i). A difference between a data index of the i-th peak P(i) and a data index of the (i+1)-th peak P(i+1) is obtained and then multiplied by a sampling rate to define a time interval. For example, when the data index of the i-th peak P(i) is i(n) and the data index of the (i+1)-th peak P(i+1) is i(n+k), PPI(i) can be expressed by Formula (1) as follows:

$$PPI(i) = [i(n+k) - i(n)] \times \text{sampling rate} \quad (1)$$

In association with the PPI 63, an average PPI and a total number of PPIs per a predetermined period of time are defined. In the total number of PPIs, the number of PPIs less than the average PPI is defined as a "fast PPI count". A ratio of the fast PPI count to the total number of PPIs is defined as a "fast PPI count %". A value obtained by subtracting the fast PPI count % from 100 is defined as a "slow PPI count %".

Next, a baseline spread range 65 is defined by a difference between a maximum peak Pmax and a minimum peak Pmin in the entire PPG data collected per a predetermined period of time.

Referring to back to FIG. 5, in step 53, a predetermined period of time is set as a unit time, and PPG data is collected during the unit time. For this operation, a PPG measuring device shown in FIG. 7A or 7B is used.

Figure 7A:
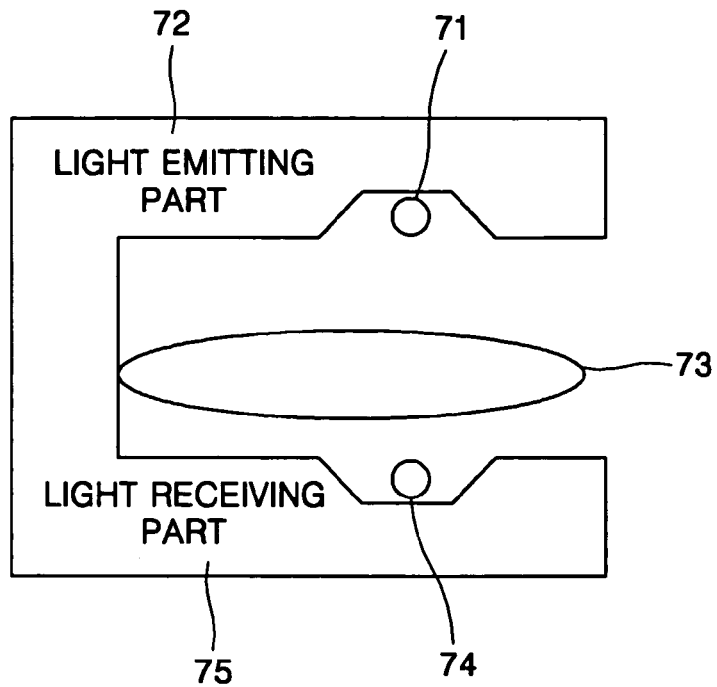
FIGS. 7A and 7B are diagrams of examples of a PPG measuring device used to acquire PPG data in the method shown in FIG. 5.
Figure 7B:
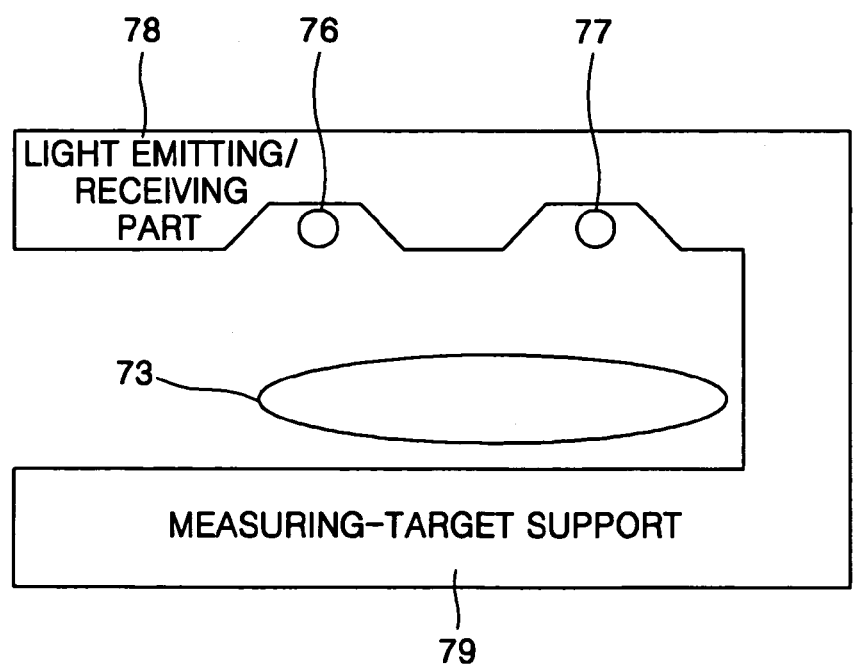
Figure 8A:
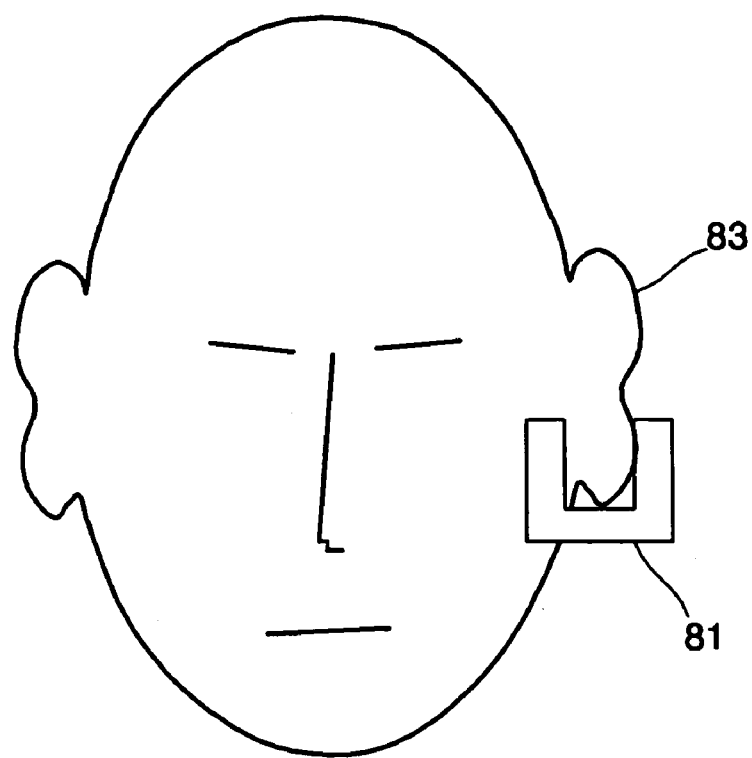
FIGS. 8A and 8B are diagrams showing usage examples of the PPG measuring devices shown in FIGS. 7A and 7B.
Figure 8B:
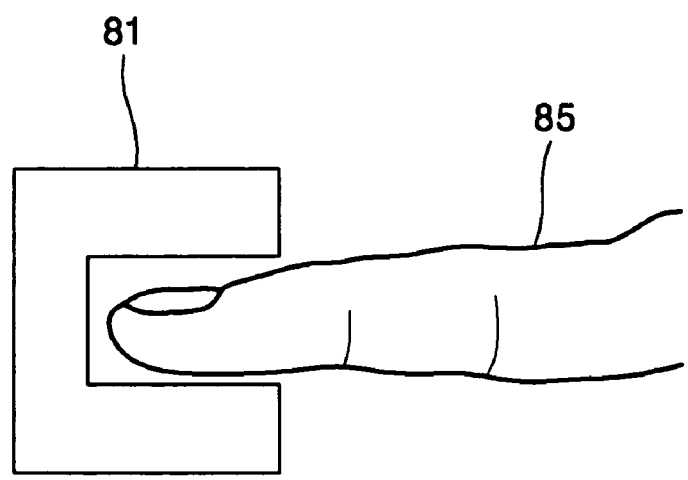

FIG. 7A shows a transmissive PPG measuring device including a light emitting part 72 with a light emitting element 71 radiating light and a light receiving part 75 with a light receiving element 74 detecting light transmitted by a measuring target 73. The housings of the light emitting part 72 and the light receiving part 75 are connected at one end to form a block letter "C" shape. FIG. 7B shows a reflective PPG measuring device including a light emitting/receiving part 78 with a light emitting element 76 for radiating light and a light receiving element 77 for detecting light reflected from a measuring target 73. A measuring target support 79 is connected to one end of the light emitting/receiving part 78 to form a block letter "C" shape. As shown in FIGS. 8A and 8B, a PPG measuring device 81, such as shown in FIG. 7A or 7B, may be used at any part of a human body, for example, an ear 83, a finger 85, or a toe.

In step 53 of the method shown in the flowchart of FIG. 5, light having a particular wavelength is radiated at the measuring target 73 of a human body using the PPG measuring device 81, and light reflected or transmitted by the measuring target 73 is detected. Here, light used in the light emitting part 72 or 78 has a particular wavelength well-suited to the purpose of measurement, such as a wavelength of between about 500-1000 nm, and may have a single wavelength or two or more wavelengths. A data sampling frequency is selected to be in an appropriate range considering a highest frequency in PPG so that an aliasing phenomenon or distortion of an original signal may be avoided. A data sampling time may be preferably set to be at least 30 seconds but may be alternately set to be appropriate depending on a purpose of the measurement.

In step 55, low-pass filtering is performed in order to remove high-frequency noise from the PPG data collected in step 53. In this step, a low-pass filter having a 10 Hz cut-off frequency may be used.

In step 57, the PPG data filtered in step 55 is analyzed using the PPG parameters defined in step 51 to calculate a human subject's stress index. Step 57 will be described in detail with reference to FIG. 9.

Figure 9:
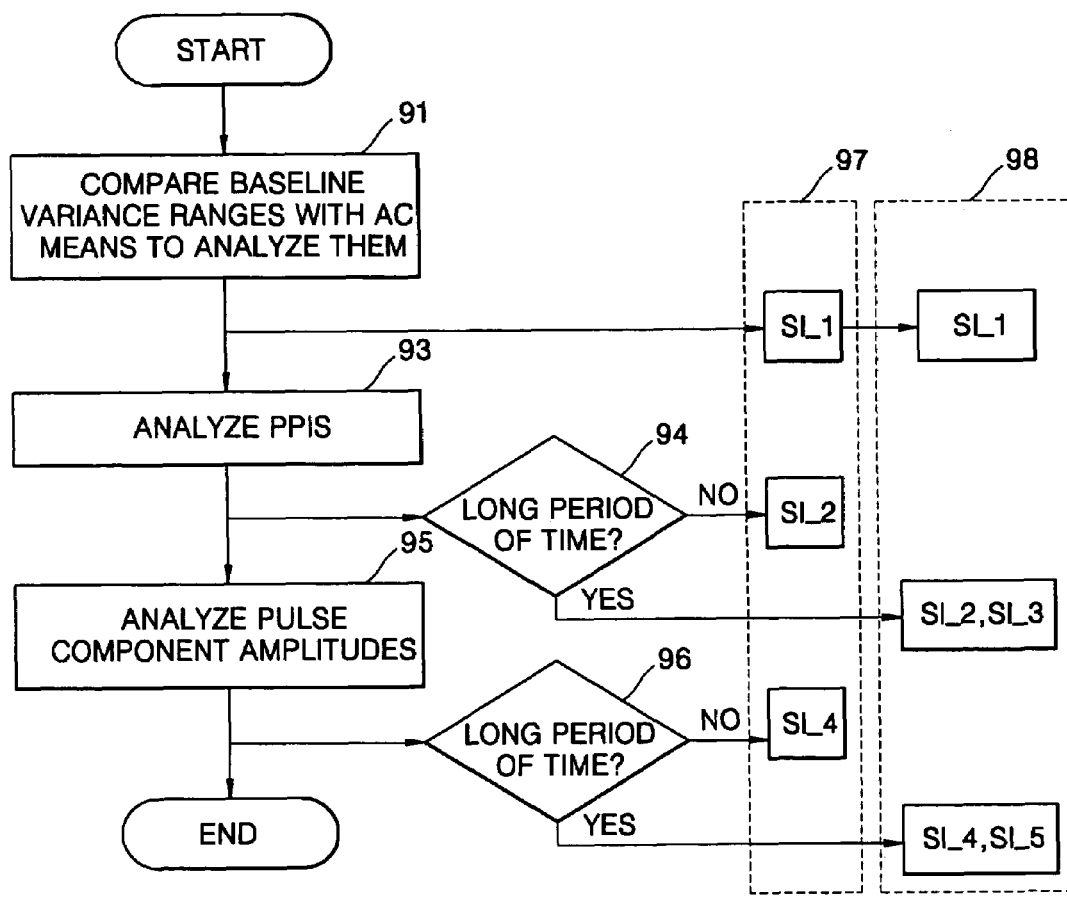
FIG. 9 is a detailed flowchart of analysis of the method shown in FIG. 5.

Referring to FIG. 9, in step 91, a baseline spread range is compared with an AC mean to obtain a stress index SI. For example, stress indexes are classified into eight (8) classes according to conditional formulae shown in Table 3. If a data group to be compared satisfies a condition for a particular class among the eight (8) classes, subtraction or addition is performed on a stress index SI in accordance with the condition. The stress index obtained as the result of the above operation is referred to as SI_1 and is adjusted so as not to exceed 100.

TABLE 3

| Class | Condition | Stress index (initial value = 30) |
|---|---|---|
| A | AC mean*3 ≦ baseline spread range | SI = SI − 20 |
| B | AC mean*3 < baseline spread range ≦ AC mean*4 | SI = SI + 5 |
| C | AC mean*4 < baseline spread range ≦ AC mean*5 | SI = SI + 15 |
| D | AC mean*5 < baseline spread range ≦ AC mean*6 | SI = SI + 20 |
| E | AC mean*6 < baseline spread range ≦ AC mean*7 | SI = SI + 30 |
| F | AC mean*7 < baseline spread range ≦ AC mean*8 | SI = SI + 40 |
| G | AC mean*8 < baseline spread range ≦ AC mean*9 | SI = SI + 50 |
| H | AC mean*9 < baseline spread range | SI = SI + 60 |

In step 93, a fast PPI count % is calculated based on an average PPI, and it is determined whether the fast PPI count % is within a predetermined range to obtain a stress index SI. For example, stress indexes are classified into three (3) classes according to conditional formulae shown in Table 4. If a data group to be compared satisfies a condition for a particular class among the three (3) classes, subtraction or addition is performed on a stress index SI in accordance with the condition. The stress index obtained as the result of the above operation is referred to as SI_2 and is adjusted so as not to exceed 100.

TABLE 4

| Class | Condition | Stress index (initial value = 50) |
|---|---|---|
| A | fast PPI count % ≦ 50 | SI = SI − 20 |
| B | 50 < fast PPI count % ≦ 60 | SI = SI + 15 |
| C | 60 < fast PPI count % | SI = SI + 35 |

In addition, if, in step 94, it is determined that a long period of time was required to collect PPG data, a statistical method can be used in order to increase the reliability of evaluation. For example, when it takes more than one minute to collect PPG data, it is determined whether a total number of PPIs in the collected PPG data is at least fifty (50). If it is determined that the total number of PPIs is at least fifty (50), a PPI time series data group from an initial PPI to a 25th PPI is defined as a first data group, dataset_1, a PPI time series data group corresponding to the next twenty-five (25) PPIs is defined as a second data group, dataset_2. An n-th data group, dataset_n is defined in the same manner. If there are two data groups to be compared, a two-sample paired t-test is performed to detect a p-value. If there are at least three data groups to be compared, one-way ANalysis Of VAriance (ANOVA) is performed to detect a p-value. If the detected p-value is greater than 0.05, a stable condition is determined. If the detected p-value is smaller than 0.05, an unstable condition is determined. In addition, determination of a degree of stress based on a p-value can be more precisely performed on the basis of 0.05. For example, stress indexes are classified into four (4) classes according to conditional formulae shown in Table 4. If a data group to be compared satisfies a condition for a particular class among the four (4) classes, subtraction or addition is performed on a stress index SI in accordance with the condition. The stress index obtained as the result of the above operation is referred to as SI_3 and is adjusted so as not to exceed 100.

TABLE 5

| Class | Condition | Stress index (initial value = 50) |
|---|---|---|
| A | p-value ≧ 0.05 | SI = SI − 20 |
| B | 0.01 ≦ p-value < 0.05 | SI = SI + 15 |
| C | 0.001 ≦ p-value < 0.01 | SI = SI + 25 |
| D | p-value < 0.001 | SI = SI + 35 |

Next, in step 95, a small AC count % is calculated based on an AC mean, and it is determined whether the small AC count % exists within a predetermined range in order to obtain a stress index SI. For example, stress indexes are classified into three (3) classes according to conditional formulae shown in Table 6. If a data group to be compared satisfies a condition for a particular class among the three (3) classes, subtraction or addition is performed on a stress index SI in accordance with the condition. The stress index obtained as the result of the above operation is referred to as SI_4 and is adjusted so as not to exceed 100.

TABLE 6

| Class | Condition | Stress index (initial value = 50) |
|---|---|---|
| A | small AC count % ≦ 50 | SI = SI − 20 |
| B | 50 < small AC count % ≦ 60 | SI = SI + 15 |
| C | 60 < small AC count % | SI = SI + 35 |

In addition, if in step 96, it is determined that a long period of time was required to collect PPG data, a statistical method can be used in order to increase the reliability of evaluation. For example, when it takes more than one minute to collect PPG data, it is determined whether a total number of pulse components in the collected PPG data is at least fifty (50). If it is determined that the total number of pulse components is at least fifty (50), a pulse component amplitude time series data group from an initial pulse component to a 25th pulse component is defined as a first data group, dataset_1, a pulse component amplitude time series data group corresponding to the next twenty-five (25) pulse components is defined as a second data group, dataset_2. An n-th data group, dataset_n, is defined in the same manner. If there are two data groups to be compared, a two-sample paired t-test is performed to detect a p-value. If there are three or more data groups to be compared, one-way ANOVA is performed to detect a p-value. If the detected p-value is greater than 0.05, a stable condition is determined. If the detected p-value is smaller than 0.05, an unstable condition is determined. In addition, determination of a degree of stress based on a p-value can be more precisely performed on the basis of 0.05. For example, stress indexes are classified into four (4) classes according to conditional formulae shown in Table 7. If a data group to be compared satisfies a condition for a particular class among the four (4) classes, subtraction or addition is performed on a stress index SI in accordance with the condition. The stress index obtained as the result of the above operation is referred to as SI_5 and is adjusted so as not to exceed 100.

TABLE 7

| Class | Condition | Stress index (initial value = 50) |
|---|---|---|
| A | p-value ≧ 0.05 | SI = SI − 20 |
| B | 0.01 ≦ p-value < 0.05 | SI = SI + 15 |
| C | 0.001 ≦ p-value < 0.01 | SI = SI + 25 |
| D | p-value < 0.001 | SI = SI + 35 |

As described above, short-term stress indexes and long-term stress indexes can be obtained depending on time taken for collecting PPG data. A short-term stress index group 97 includes SI__1, SI__2, and SI__4, and a long-term stress index group 98 includes SI__1, SI__2, SI__3, SI__4, and SI__5. After setting maximum values for the respective stress indexes SI__1 through SI__5, a degree of stress can be evaluated based on the set values. For example, a maximum value of each of the stress indexes SI__1 through SI__5 can be set to an exemplary 100 to facilitate explanation, and a degree of stress, which is referred to as a stress index %, may be calculated as shown in Formulae (2) and (3).

$$\text{Long-term stress index \%} = (\text{sum of long-term stress indexes}/300)*100 \quad (2)$$

$$\text{Short-term stress index \%} = (\text{sum of short-term stress indexes}/500)*100 \quad (3)$$

More specifically, in step 57 of FIG. 5, the PPG data is divided into a long-term test and a short-term test, depending on an amount of time taken to collect the PPG data, and separately analyzed. For example, data may be placed under the short-term test when a data collection time is less than one minute, and data may be placed under the long-term test when a data collection time exceeds one minute.

Figure 10:
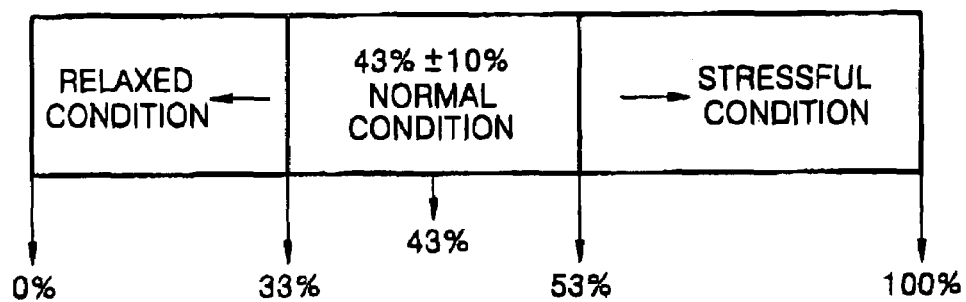
FIG. 10 is a diagram showing an example of displaying stress based on the distribution of degrees of stress in the method shown in FIG. 5.

Referring back to FIG. 5, in step 59, items of the stress indexes detected in step 57 and a final stress index % are displayed. The stress index items may be changed when necessary. When it is determined whether the stress index % exists within a predetermined reference range, the stress index % may be displayed along with the predetermined reference range. For example, the stress index % may be evaluated based on a distribution thereof, as shown in FIG. 10. More specifically, when the stress index % is within a range of ±10% centering around 43%, a normal condition is determined. When the stress index % exceeds the maximum limit of the normal range, a stressful condition is determined. When the stress index % is less than the minimum limit of the normal range, a relaxed condition is determined.

Figure 11:
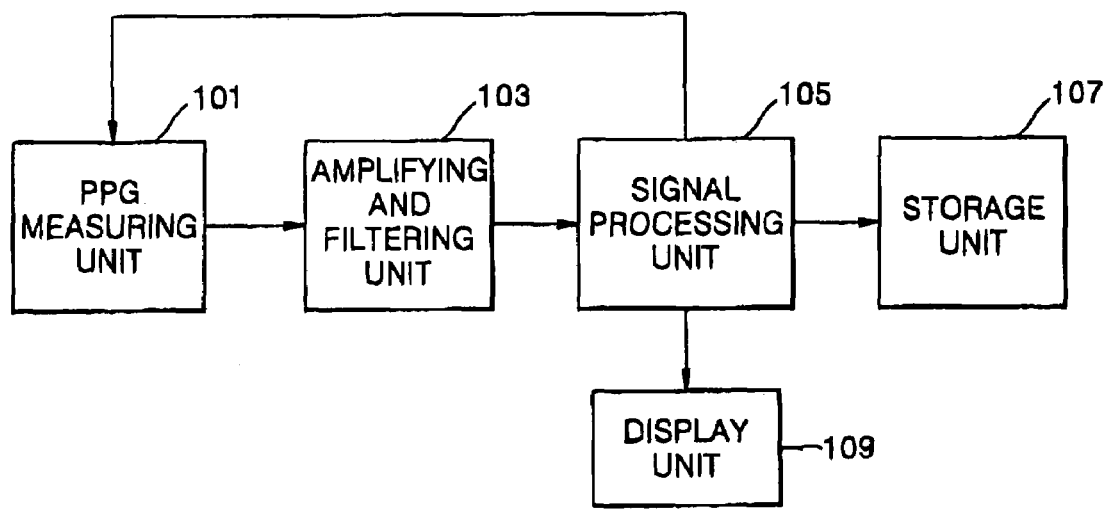
FIG. 11 is a block diagram of an apparatus for evaluating human stress using PPG according to an embodiment of the present invention.

FIG. 11 is a block diagram of an apparatus for evaluating human stress using PPG according to an embodiment of the present invention. The apparatus includes a PPG measuring unit 101, an amplifying and filtering unit 103, a signal processing unit 105, a storage unit 107, and a display unit 109.

Referring to FIG. 11, the PPG measuring unit 101 has a block letter "C" shape, as shown in FIG. 7A or 7B, so that a measuring target may be inserted into the PPG measuring unit 101. The PPG measuring unit 101 measures a PPG signal generated from a part of a human body, such as a finger, toe, or earlobe, where peripheral blood vessels are concentrated. An on/off interval of the PPG measuring unit 101 is controlled by the signal processing unit 105. The amplifying and filtering unit 103 amplifies the PPG signal provided from the PPG measuring unit 101 to a predetermined level and performs filtering to remove noise components.

The signal processing unit 105 extracts a PPG signal reacting to a particular blood component from a signal provided from the amplifying and filtering unit 103, converts the extracted PPG signal to digital data, calculates pulse component amplitudes, a baseline spread range, and PPIs with respect to the PPG digital data during a predetermined period of time, and evaluates human stress using the calculated PPG parameters. A program for performing a method of evaluating human stress using PPG according to the present invention is recorded in the signal processing unit 105, and a computer-readable recording medium is installed therein.

The storage unit 107 stores the processing result from the signal processing unit 105. The display unit 109 displays the processing result from the signal processing unit 105 to report the result to a user.

In addition, an apparatus for evaluating human stress using PPG according to the present invention may employ a wireless communication mode so that the PPG measuring unit 101 transmits and receives data to and from a receiving side without being connected to a PC. Alternatively, although a wireless communication mode is not employed, since extraction of reliable parameters in the PPG measuring unit 101 simplifies an algorithm and reduces an amount of arithmetic operation, an apparatus of the present invention can be implemented in a stand alone unit, in which the PPG measuring unit 101 and the signal processing unit 105 coexist.

The present invention may be realized as a code that is recorded on a computer-readable recording medium and can be read by a computer. For example, a method of evaluating human stress using PPG according to the present invention may be implemented by recording on a computer-readable recording medium a first program for defining PPG parameters including at least one of a pulse component amplitude, a PPI, and a baseline spread range; a second program for radiating light having at least one wavelength, which reacts to a blood component to be measured, at a measuring target and measuring a PPG signal from the measuring target for a predetermined period of time; and a third program for evaluating a level of human stress based on the PPG parameters defined by the first program, in a long-term test or a short-term test identified depending on a measuring time of the PPG signal.

The computer-readable recording medium may be any type on which data that can be read by a computer system can be recorded, for example, a ROM, a RAM, a CD-ROM, a magnetic tape, a floppy disc, or an optical data storage device. The present invention may also be realized as carrier waves (for example, transmitted through the Internet). Alternatively, computer readable recording media may be distributed among computer systems connected through a network so that the present invention can be realized as a code that is stored in the recording media and can be read and executed in the computers. Functional programs, codes, and code segments for implementing the present invention may be easily inferred by programmers skilled in the art of the present invention.

As described above, according to the present invention, a level of a human subject's stress is determined using an average of pulse component amplitudes, i.e., an AC mean, an average PPI, and a baseline spread range that are defined with respect to a PPG signal, so that a human subject may be inconvenienced as little as possible, and the reliability of analysis may also be increased.

In addition, according to the present invention, a PPG measuring device may be simplified and miniaturized so that a PPG signal can be measured from any body part where peripheral blood vessels are concentrated, such as an earlobe or a finger. As a result, even when a human subject is working on a PC, a degree of stress can be continuously measured over a long period of time.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of evaluating human stress using photoplethysmography (PPG), comprising:
   defining at least one PPG parameter;
   radiating light having at least one wavelength, which reacts to a blood component to be measured, at a measuring target and measuring a PPG signal from the measuring target during a predetermined period of time; and
   evaluating a level of human stress using a plurality of relative stress indexes obtained from the PPG parameter, wherein evaluating the level of human stress includes:
   obtaining an average of pulse component amplitudes during a predetermined period of time;
   comparing a baseline spread range with the average of pulse component amplitudes during the predetermined period of time;
   calculating a first relative stress index based on a relationship between the baseline spread range and the average of pulse component amplitudes.

2. The method as claimed in claim 1, wherein the at least one PPG parameter includes at least one a pulse component amplitude, a peak-to-peak interval, and a baseline spread range.

3. The method as claimed in claim 2, wherein evaluating the level of human stress comprises using one of a long-term test and a short-term test.

4. The method as claimed in claim 1, further comprising:
   performing low-pass filtering to remove high-frequency noise from the measured PPG signal, before evaluating the level of human stress.

5. The method as claimed in claim 3, wherein evaluating the level of human stress in the short-term test comprises:
   obtaining an average of peak-to-peak intervals during a predetermined period of time;
   counting a number of peak-to-peak intervals less than the average peak-to-peak interval and a number of peak-to-peak intervals greater than the average peak-to-peak interval, during the predetermined period of time; and
   calculating a second relative stress index of the plurality of relative stress indexes based on a relationship between the number of peak-to-peak intervals less than the average peak-to-peak interval and the number of peak-to-peak intervals greater than the average peak-to-peak interval.

6. The method as claimed in claim 3, wherein evaluating the human stress in the long-term test comprises:
   obtaining peak-to-peak intervals with respect to all pulses during a predetermined period of time;
   defining a plurality of data groups composed of a predetermined number of peak-to-peak intervals with respect to all of the peak-to-peak intervals obtained during the predetermined period of time;
   performing a predetermined statistical method according to a number of the plurality of data groups; and
   calculating a third relative stress index of the plurality of relative stress indexes based on a p-value detected as a result of performing the predetermined statistical method.

7. The method as claimed in claim 3, wherein evaluating the level of human stress in the short-term test comprises:
   counting a number of pulse components having an amplitude less than the average of pulse component amplitudes and a number of pulse components having an amplitude greater than the average of pulse component amplitudes, during the predetermined period of time; and
   calculating a fourth relative stress index of the plurality of the relative stress indexes based on a relationship between the number of pulse components having an amplitude less than the average of pulse component amplitudes and the number of pulse components having an amplitude greater than the average of pulse component amplitudes.

8. The method as claimed in claim 3, wherein evaluating the level of human stress in the long-term test comprises:
   obtaining pulse component amplitudes with respect to all pulses during a predetermined period of time;
   defining a plurality of data groups composed of a predetermined number of pulse component amplitudes with respect to all of the pulse component amplitudes obtained during the predetermined period of time;
   performing a predetermined statistical method according to a number of the plurality of data groups; and
   calculating a third relative stress index based on a p-value detected as a result of performing the predetermined statistical method.

9. The method as claimed in claim 6, wherein the predetermined statistical method is a two-sample paired t-test when the number of the plurality of data groups is two and is one-way ANalysis Of VAriance (ANOVA) when the number of the plurality of data groups is three or more.

10. The method as claimed in claim 8, wherein the predetermined statistical method is a two-sample paired t-test when the number of the plurality of data groups is two and is one-way ANalysis Of VAriance (ANOVA) when the number of the plurality of data groups is three or more.

11. The method as claimed in claim 5, wherein evaluating the level of human stress further comprises:
   counting a total number of pulse components, a number of pulse components having an amplitude less than the average of pulse component amplitudes, and a number of pulse components having an amplitude greater than the average of pulse component amplitudes, during the predetermined period of time; and
   calculating a fourth relative stress index of the plurality of relative stress indexes based on a relationship between the number of pulse components having an amplitude less than the average of pulse component amplitudes and the number of pulse components having an amplitude greater than the average of pulse component amplitudes.

12. The method as claimed in 1, further comprising displaying the plurality of relative stress indexes and the evaluated level of human stress obtained during evaluating the level of human stress.

13. The method as claimed in claim 1, further comprising:
   averaging the plurality of relative stress indexes acquired using at least one PPG parameter; and
   determining an average stress index as a final stress index.

14. A computer-readable recording medium, comprising:
   a first program for defining photoplethysmography (PPG) parameters including at least one of a pulse component amplitude, a peak-to-peak interval, and a baseline spread range recorded on the medium;
   a second program for radiating light having at least one wavelength, which reacts to a blood component to be measured, at a measuring target and measuring a PPG signal from the measuring target for a predetermined period of time recorded on the medium;

a third program for evaluating a level of human stress using a plurality of relative stress indexes based on the PPG parameters defined by the first program, in one of a long-term test and a short-term test, which are identified depending on a measuring time of the PPG signal, recorded on the medium;

a fourth program for obtaining an average of pulse component amplitudes during a predetermined period of time;

a fifth program for comparing a baseline spread range with the average of pulse component amplitudes during the predetermined period of time; and a sixth program for calculating a first relative stress index based on a relationship between the baseline spread range and the average of pulse component amplitudes.

15. The computer-readable recording medium as claimed in claim 14, further comprising:

a seventh program for displaying the plurality of relative stress indexes and the evaluated level of human stress obtained during evaluating the level of human stress.

16. An apparatus for evaluating human stress using photoplethysmography (PPG), comprising:

a PPG measuring unit, which radiates light having at least one wavelength, which reacts to a blood component to be measured, at a measuring target and measures a PPG signal from the measuring target during a predetermined period of time;

an amplifying and filtering unit, which amplifies the PPG signal provided from the PPG measuring unit to a predetermined level and performs filtering to remove noise components;

a signal processing unit which defines at least one PPG parameter and evaluates a level of human stress using a plurality of relative stress indexes acquired using the PPG parameter the signal processing unit including a first function of obtaining an average of pulse component amplitudes and an average peak-to-peak interval during the predetermined period of time, a second function of comparing a baseline spread range with the average of pulse component amplitudes during the predetermined period of time, and a third function of calculating a first relative stress index of the plurality of relative stress indexes based on a relationship between the baseline spread range and the average of pulse component amplitudes.

17. An apparatus as claimed in claim 16, wherein the signal processing unit comprises:

a display unit configured to display the level of human stress evaluated by the signal processing unit.

18. The apparatus as claimed in claim 16, wherein the PPG parameter includes at least of a pulse component amplitude, a peak-to-peak interval, and a baseline spread range.

19. The apparatus as claimed in claim 16, wherein the level of human stress is acquired from one of a long-term test and a short-term test, which are identified depending on a measuring time of the PPG signal provided from the amplifying and filtering unit.

20. An apparatus as claimed in claim 19, wherein the signal processing unit further comprises:

a ninth function of obtaining peak-to-peak intervals with respect to all pulses during a predetermined period of time;

a tenth function of defining a plurality of data groups composed of a predetermined number of peak-to-peak intervals with respect to all of the peak-to-peak intervals obtained during the predetermined period of time;

an eleventh function of performing a predetermined statistical method according to a number of the plurality of data groups; and a twelfth function of calculating a third relative stress index of the plurality of relative stress indexes based on a p-value detected as a result of performing the predetermined statistical method.

21. An apparatus as claimed in claim 19, wherein the signal processing unit further comprises:

a thirteenth function of obtaining pulse component amplitudes with respect to all pulse during a predetermined period of time;

a fourteenth function of defining a plurality of data groups composed of a predetermined number of pulse component amplitudes with respect to all of the pulse component amplitudes obtained during the predetermined period of time;

a fifteenth function of performing a predetermined statistical method according to a number of the plurality of data groups; and a sixteenth function of calculating a third relative stress index based on a p-value detected as a result of performing the predetermined statistical method.

22. The apparatus as claimed in claim 16, wherein the first function further includes obtaining an average peak-to-peak interval during the predetermined period of time, and the signal processing unit further comprises:

a fourth function of counting a total number of peak-to-peak intervals, a number of peak-to-peak intervals less than the average peak-to-peak interval, and a number of peak-to-peak intervals greater than the average peak-to-peak interval, during the predetermined period of time; and a fifth function of calculating a second relative stress index of the plurality of relative stress indexes based on a relationship between the number of peak-to-peak intervals less than the average peak-to-peak interval and the number of peak-to-peak intervals greater than the average peak-to-peak interval.

23. The apparatus as claimed in claim 16, wherein the signal processing unit further comprises:

a sixth function of counting a total number of pulse components, a number of pulse components having an amplitude less than the average of pulse component amplitudes, and a number of pulse components having an amplitude greater than the average of pulse component amplitudes, during the predetermined period of time; and a seventh function of calculating a third relative stress index of the plurality of relative stress indexes based on a relationship between the number of pulse components having an amplitude less than the average of pulse component amplitudes and the number of pulse components having an amplitude greater than the average of pulse component amplitudes.

24. The apparatus as claimed in claim 16, wherein the signal processing unit further comprises:

an eighth function of averaging the plurality of relative stress indexes acquired using the PPG parameter and determining an average stress index as a final stress index.

* * * * *